United States Patent [19]

Rose

[11] Patent Number: 4,506,542

[45] Date of Patent: Mar. 26, 1985

[54] APPARATUS AND PROCEDURE FOR RELATIVE PERMEABILITY MEASUREMENTS

[75] Inventor: Walter D. Rose, Denver, Colo.

[73] Assignee: Chandler Engineering Company, Tulsa, Okla.

[21] Appl. No.: 487,768

[22] Filed: Apr. 22, 1983

[51] Int. Cl.³ ............................................. G01N 15/08
[52] U.S. Cl. .................................................... 73/38
[58] Field of Search ................................. 73/38, 37

[56] References Cited

U.S. PATENT DOCUMENTS

| | | |
|---|---|---|
| 2,293,488 | 8/1942 | Bays . |
| 2,345,935 | 4/1944 | Hassler ................................ 73/38 |
| 2,390,252 | 12/1945 | Hayward ............................ 73/38 |
| 2,539,355 | 1/1951 | Reichertz ........................... 73/38 |
| 2,618,151 | 11/1952 | Leas .................................... 73/38 |
| 2,705,418 | 4/1955 | Reichertz et al. ................ 73/38 |
| 2,724,693 | 11/1955 | Brink .................................. 73/38 |
| 2,737,804 | 3/1956 | Herzog et al. .................... 73/38 |
| 2,821,680 | 1/1958 | Slusser et al. ..................... 73/38 |
| 3,139,747 | 7/1964 | Ferrell et al. ..................... 73/38 |
| 3,140,599 | 7/1964 | Rahme et al. .................... 73/38 |
| 3,172,285 | 3/1965 | Dietert et al. .................... 73/38 |
| 3,180,133 | 4/1965 | Rahme ............................... 73/38 |
| 3,405,553 | 10/1968 | Boisard et al. . |
| 3,548,634 | 12/1970 | Roy ..................................... 73/38 |
| 3,590,634 | 7/1971 | Pasternak et al. ............... 73/38 |
| 4,052,885 | 10/1977 | Shuck ................................. 73/38 |
| 4,064,740 | 12/1977 | Crosby ............................... 73/38 |
| 4,311,037 | 1/1982 | Gotchel et al. .................. 73/38 |

FOREIGN PATENT DOCUMENTS 2650643  9/1978  Fed. Rep. of Germany .......... 73/38

OTHER PUBLICATIONS

Rose, Walter, "Some Problems in Applying the Hassler Relative Permeability Method", 32 Journal of Petroleum Technology Forum, 1161–63, (Jul. 1980).

Rose, Walter, "Some Problems of Relative Permeability Measurement", Proceedings of the Third World Petroleum Congress, The Hague, Sect. II, 446–59, (1951).

Scheidegger, Adrian, The Physics of Flow through Porous Media, pp. 250–255, (3rd ed., Univ. of Toronto Press).

*Primary Examiner*—Stewart J. Levy
*Assistant Examiner*—Hezron E. Williams
*Attorney, Agent, or Firm*—Finnegan, Henderson, Farabow, Garrett & Dunner

[57] ABSTRACT

An apparatus for determining data from which to calculate relative permeability of a porous body to a first fluid and a second fluid comprising a holder that renders all but first and second outer faces of the porous body impermeable to the first and second fluids. First and second capillary barriers respectively cover the first and second outer surfaces of the porous body. The barriers are permeable to the first fluid and impermeable to the second fluid. A first fluid flow system brings the first fluid to the outer surface of the first porous barrier, flows the first fluid under pressure through the first porous barrier, the porous body and the second porous barrier, and carries the first fluid away from the outer surface of the second capillary barrier. A second fluid flow system flows the second fluid under pressure through the porous body and carries the second fluid away from the second outer surface of the porous body. The pressure of the first fluid downstream of the porous body and the flow rate of the first fluid are held constant while the saturation level of the second fluid in the porous body is varied. Data obtained from pressure and flow rate information may be used to determine the relative permeability of the first and second fluids using Darcy's law. Method for using the apparatus.

22 Claims, 4 Drawing Figures

Fig. 3

APPARATUS AND PROCEDURE FOR RELATIVE PERMEABILITY MEASUREMENTS

BACKGROUND OF THE INVENTION

The present invention relates to a method and apparatus for determining the relative permeability of porous solids.

Relative permeability may be thought of as a useful measure of the effective hydraulic conductivity of a fluid in multiphase flow of immiscible fluid mixtures through interstitial (pore) spaces of porous solids. Each fluid phase has its own relative permeability transport coefficient. These transport coefficients depend on many factors such as whether the particular fluid is wetting or nonwetting with respect to the particular porous solid, the saturation level of the fluid in the body, the partitioning of the pore space among fluids in multiphase flow, and the pore space geometry.

Relative permeability data are important in many areas. For example, relative permeability is extremely important in determining the parameters used in computer simulation of oil recovery systems and in the geochemical field generally.

In a porous body, capillary attraction is a function of the forces of adhesion between a liquid and a solid, and the forces of cohesion of the liquid to itself. A liquid that wets a solid has greater forces of adhesion to the particular solid than does a non-wetting fluid. A fluid may wet one solid and not another solid. A particular fluid may also be wetting or nonwetting in relation to other fluids when considering a single solid. Thus, in multiphase flow, if the force of adhesion of a first fluid for a porous body is greater than the force of adhesion of a second fluid for a porous body, then the first fluid will be considered a wetting fluid for a porous body in relation to the second fluid, even though the force of adhesion for the solid in the first fluid is not as great as the force of cohesion of that first fluid for itself.

The saturation level of a given liquid in a porous body, S, is a value between 0 and 1 that shows the fraction of the available pore space occupied by a particular fluid under consideration. A saturation level of 1 indicates that in a given porous body the entire available pore space is filled by the fluid under consideration. Both a local saturation level within a pore and an overall saturation level within a porous body may be relevant variables.

In a porous body containing two or more immiscible fluids, the local pore space may be partitioned among these fluids differently at each saturation level. For example, one fluid may adhere strongly to the surfaces within a given pore while another may have no effective contact with the solid material. Moreover, the local pore space geometry may vary dramatically within a given porous body.

Of the several relative permeability measurement schemes that have been described in the literature, U.S. Pat. No. 2,345,935 to Hassler is, conceptually at least, superior to other proposed methods, for example U.S. Pat. No. 2,390,252 to Hayward. Unfortunately, however, Hassler's method has many operating difficulties. Most importantly, the Hassler technique involves determination of internal wetting fluid pressures within the porous body. See, e.g., W. Rose, "Some Problems in Applying the Hassler Relative Permeability Method," 32 *J. Petroleum Technology*, 1161-63 (July, 1980).

SUMMARY OF THE INVENTION

The principal object of the present invention therefore is to provide a method and apparatus that are free of the limitations of Hassler's method and apparatus, and yet provide creditable relative permeability data. The present invention is directed to curing the difficulties with Hassler's method and apparatus by providing a method and apparatus that do not require measurement of internal fluid pressures for accurate data.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides an apparatus for determining data from which to calculate relative permeability of a porous body to a first fluid and a second fluid comprising: (a) means for rendering all but first and second outer surfaces of the porous body impermeable to the first and second fluid; (b) first and second capillary barriers respectively covering the first and second outer surfaces, the barriers being permeable to the first fluid and impermeable to the second fluid; (c) first fluid inlet means for flowing the first fluid under pressure to an outer surface of the first barrier and first fluid outlet means for conducting the first fluid away from an outer surface of the second barrier; (d) means for controllably changing the pressure of the first fluid; (e) means for maintaining constant the flow rate of the first fluid; (f) second fluid inlet means for flowing the second fluid under pressure to the first surface of the porous body and second fluid outlet means for conducting the second fluid away from the second surface of the porous body; (g) means for gauging the pressure of the first fluid at the first fluid inlet means and at the first fluid outlet means; (h) means for maintaining constant the fluid pressure at the first fluid outlet means; (i) means for gauging the fluid pressure at the second fluid inlet means and at the second fluid outlet means; and (j) means for regulating fluid pressure at the second fluid inlet means for the second fluid outlet means.

To further achieve the foregoing objects and in accordance with the purpose of the invention, the invention further provides a method for determining data from which to calculate relative permeability of a porous body to first fluid flow and second fluid flow comprising the steps of: (a) saturating the porous body with the first fluid; (b) forcing the first fluid to flow under pressure through the porous body; (c) establishing a constant pressure of the first fluid upon exiting the porous body; (d) establishing a constant flow rate of the first fluid through the porous body; (e) measuring the first fluid before the first fluid enters the porous body; (f) measuring the pressure of the first fluid after the first fluid leaves the porous body; (g) flowing the second fluid under pressure through the porous body, while maintaining constant the pressure of the first fluid and maintaining constant the flow rate of the first fluid through the porous body; (h) measuring the pressure change of the first fluid across the porous body; (i) determining the pressure of the second fluid before the second fluid enters the porous body; (j) determining the pressure of the second fluid after the second fluid leaves the porous body; (k) measuring the flow rate of the second fluid through the porous body; (l) measuring the saturation level of the second fluid; (m) increasing the saturation level of the second fluid; (n) repeating steps (g) through (m) until the saturation level of the second fluid is sufficiently high that maintaining the first fluid flow rate become impracticable; (o) decreasing the saturation level of the second fluid; and (p) repeating steps (g) through (l) and (o) until the flow rate of the second fluid equals zero.

BRIEF DESCRIPTION OF THE DRAWINGS

While this specification concludes with claims particularly pointing out and distinctly claiming that which is regarded as the present invention, the objects and advantages of this invention may be more readily ascertained from the following description of a preferred embodiment when read in conjunction with the accompanying, drawings.

DESCRIPTION OF THE PREFERRED EMBODIMENTS

Figure 1:
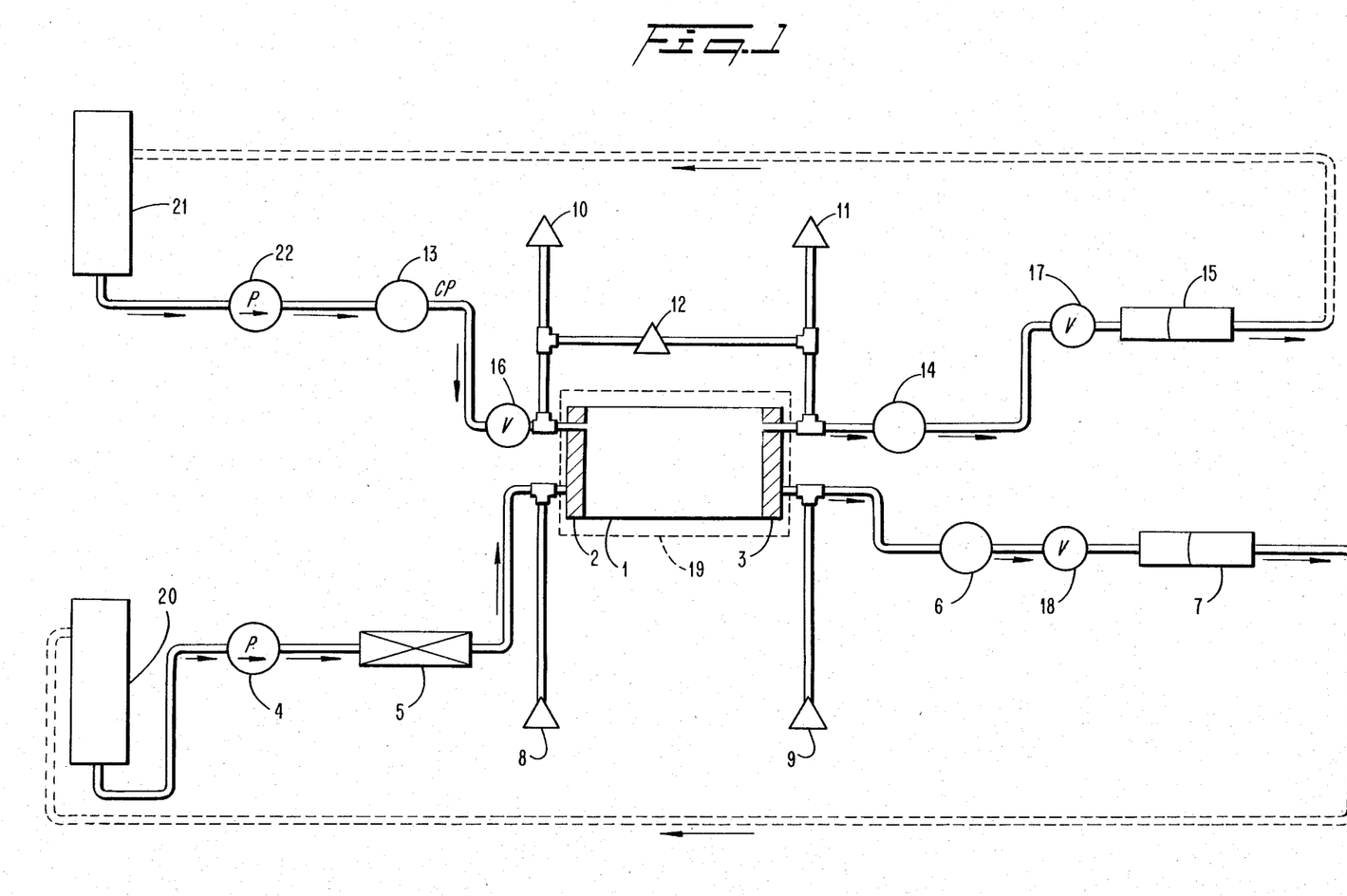
FIG. 1 is a schematic drawing of the apparatus for the invention where only two immiscible fluids move through the porous body.

Reference will now be made in detail to the presently preferred embodiments of the invention. The apparatus of the invention is shown in FIG. 1 in schematic form with a test specimen 1 included for illustration.

The apparatus comprises means for rendering all but first and second outer surfaces of the porous body impermeable to a first and second fluid. As embodied herein, for purposes of illustration, yet without implying a limitation, the means for rendering all but first and second outer surfaces of the porous body impermeable to the first and second fluid preferably comprises a rigid holder, complementary in shape to the porous body, with openings that expose the desired two outer surfaces of the porous body when the body is inserted into the holder. The holder has a small hole in the side to permit passage of a fluid under pressure. Inside the holder is a flexible lining that fits over the porous body and is impermeable to both the first and second fluids. A fluid is introduced under pressure through the small hole in the holder and fills the interstitial space between the holder and the lining. The lining is pressed against the porous body, and as long as the fluid pressure in the interstitial space is maintained, the porous body is held impermeable everywhere but at the two uncovered faces (which may be referred to as the front side and back side of the porous body, or as the first and second outer faces of the porous body). In a preferred embodiment of the invention, test speciment 1 is a right cylindrical core sample from an oil well, and the holder is a hollow cylinder with an open top and bottom.

The apparatus of the invention comprises first and second capillary barriers. As embodied herein, these barriers may comprise ceramic materials, such as unglazed Coors scientific porcelain, that are of very low permeability to prevent wetting phase breakthrough.

The invention further comprises means for controllably changing the pressure of the first fluid and, as embodied herein, the means may be any conventional means for changing pressure in a fluid, for example, a pressure regulator. The invention comprises means for maintaining the flow rate of the first fluid at a constant level, means for gauging the pressure of the first fluid at the first fluid inlet means and first fluid outlet means and the pressure of the second fluid at the second fluid inlet means and second fluid outlet means, and means for maintaining a constant fluid pressure at the first fluid outlet. As embodied herein, these means may be any conventional means such as, for example, tranducers as means for gauging pressure.

The test specimen 1 may be any porous body, but a preferred embodiment of this invention utilizes a test specimen that is a core sample of a porous rock shaped into a right-cylinder. Upstream and downstream from the test specimen 1 are semipermeable porous barriers used as capillary barriers. An upstream barrier 2 and a downstream barrier 3 are permeable to "wetting" fluids and impermeable to "nonwetting" fluids. Wetting fluid originates in a positive displacement pump 4, passes through a prefilter 5, thence through the upstream barrier 2-test specimen 1-downstream barrier 3 sandwich, and finally out through a back-pressure regulator 6 and a wetting phase flow meter 7. Inflow and outflow pressure measurements are made by transducers 8 and 9. If desired, this fluid may be recycled through the apparatus.

The "nonwetting" fluid flows through a forward pressure-controller 13, and passes directly through test specimen 1 without being blocked by porous barriers 2 and 3, and thence passes through a back-pressure control device 14 and through a flow meter 15. Upstream and downstream pressures in the nonwetting fluid portion of the flow system are measured by transducers 10 and 11, while the pressure drop between transducers 10 and 11 may, for convenience, be measured by tranducer 12. Shut-off valves 16, 17, and 18 may be available to isolate parts of the flow system, as may be pump 4 when it is not being otherwise used. The specimen holder 19 may be a Hassler core holder, and provides a seal so that the wetting and nonwetting fluid flow paths are co-linearly directed from the inflow to outflow end of the test specimen 1.

The method for delivering the wetting fluid to the barrier 2-core 1-barrier 3 sandwich may comprise a first fluid flow system. Such a system may comprise a reservoir of wetting fluid 20, or other source of wetting fluid (not shown) and conduit means for delivering the wetting fluid, under pressure supplied by pump 4, to an outer surface of porous barrier 2. The first fluid flow system also may comprise conduit means for removing the wetting fluid from an outer surface of porous barrier 3. The wetting fluid may be discarded or optionally recycled to the wetting fluid reservoir or other sources.

The method for delivering the nonwetting fluid under pressure to the porous body may comprise a second fluid flow system. Such a system may comprise a reservoir of nonwetting fluid 21, or other source of nonwetting fluid (not shown), and conduit means for delivering the nonwetting fluid to the porous barrier and a pump 22. The second fluid flow system also may comprise conduit means for removing the nonwetting fluid from a surface of the porous body in contact with barrier 3. The nonwetting fluid may be discarded or optionally recycled to the nonwetting fluid reservoir or other source.

Figure 2:
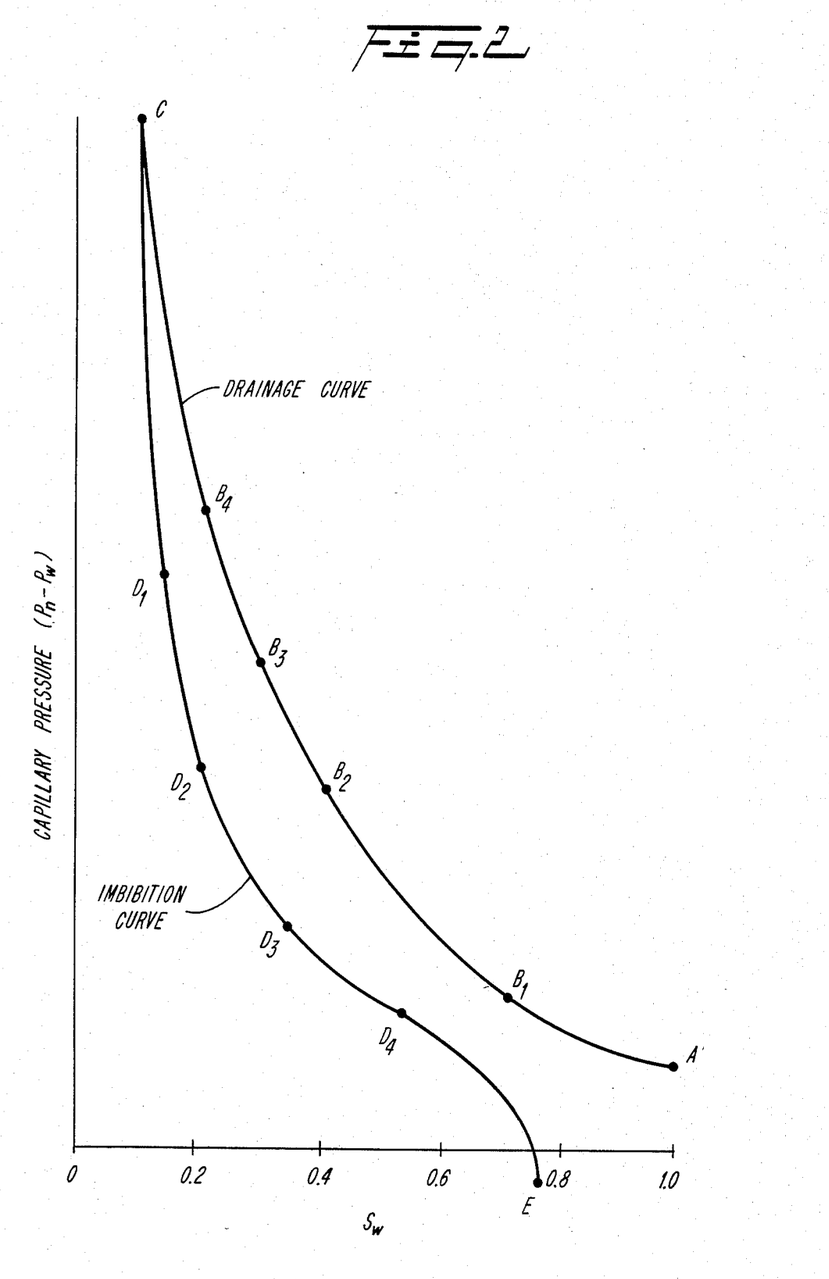
FIG. 2 is a graph demonstrating the relation between saturation and capillary pressure for a hypothetical porous body and two hypothetical immiscible fluids.

The method for using the apparatus of FIG. 1 where there are only two immiscible fluids, for example water and oil, water and gas, or oil and gas, and where the interstitial distributions at each saturation level are obtained by the well-known capillary pressure desaturation and imbibition processes may be understood by referring to FIG. 2.

To maximize the accuracy of the results from this apparatus, the flowing fluids are preferably essentially incompressible, preferably there are neither phase changes nor chemical reactions in any system of the apparatus. Preferably the porous test specimen 1 is rigid and has a pore geometry unaffected by the presence of interstitial fluids, and preferably, when steady-state conditions prevail, fluid flow is caused and controlled by imposed pressure differences only. The method and apparatus of the present invention, however, may be modified to adapt to the circumstances listed above and one skilled in the art may easily do so.

This invention may also be easily adapted to three phase flow, merely by adding appropriate additional flow systems. The intent of this disclosure is to avoid extensive and unnecessary elaboration that camouflages rather than contributes to the understanding of this invention. Thus, the preferred embodiments described herein are directed to the simple system of two immiscible fluids, rather than more complicated systems.

Test specimen 1 is saturated with the wetting fluid. The saturation level of the wetting fluid, $S_w$, is equal to 1 and the saturation level of the nonwetting fluid, $S_n$, is equal to 0. At this point, the relative permeability to the wetting phase, $K_w$, has its maximum value of 1, and the relative permeability to the nonwetting phase $K_n$, is at its minimum value, 0. The test specimen 1 and porous barriers 2 and 3 are initially saturated with the wetting fluid. The wetting fluid is delivered at a constant rate, $Q_w$, by the pump 4; the wetting fluid passes through prefilter 5, through barrier 2-core 1-barrier 3 sandwich, through back pressure control 6, and out through flow meter 7. Valves 16 and 17 are left open and the wetting fluid may escape through these ports.

Figure 3:
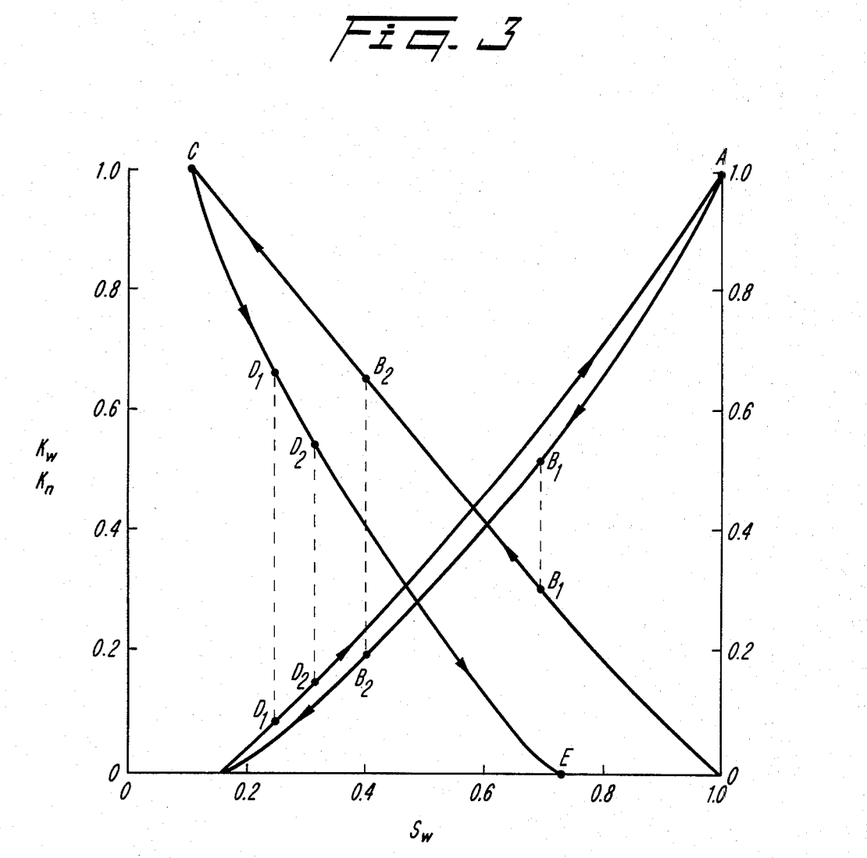
FIG. 3 is a graph of the relative permeability curves for hypothetical wetting and nonwetting fluids.

Pressure conditions are then set at regulators 13 and 14 until the wetting fluid flow through valves 16 and 17 stops. At this point the pressures read at transducers 10 and 11 will exactly balance the pressure in the wetting fluid at the inflow and outflow junctions between test specimen 1 and the surrounding barriers 2 and 3. The pressure drop of the wetting fluid across the porous body may now be read by transducer 12, and the flow rate, $Q_w$, will be given by flow meter 7 as well as by the rate of pump 4. The pressure drop is now plotted as point (A) in FIG. 2 and FIG. 3. The pressure lines of the graph in FIG. 4 for $S_w=1$ may now be derived. Sufficient information is now available to calculate the specific permeability to the wetting fluid of test specimen 1 by Darcy's Law. The sense of Darcy's Law is described, for example, in Scheidegger, *Physics of Flow Through Porous Media*, University of Toronto Press, 3rd edition, 1974, where it is shown that flow rate and pressure drop are linearly related with permeability being the constant of proportionality.

A permeability measurement for porous barriers 2 and 3 may also be made using Darcy's Law, since the geometry of these porous elements will be known as will the viscosity of the wetting fluid.

During all the succeeding steps, the pump 4 is to be manipulated so that the wetting fluid flow rate, $Q_w$, remains at the constant value established when $S_w=1$, i.e. when there was no nonwetting fluid in the system. The downstream wetting fluid pressure measured by transducer 9 is also to be held steady and invariant. The pressure in the nonwetting fluid is increased above what it had been, for example, by making careful adjustments at regulator stations 13 and 14. The new values of the nonwetting fluid pressure difference read by transducers 10 and 11 should be greater than the previous values read from these transducers by an amount equal to the desired value of capillary pressure for this stage of the experiment.

Figure 4:
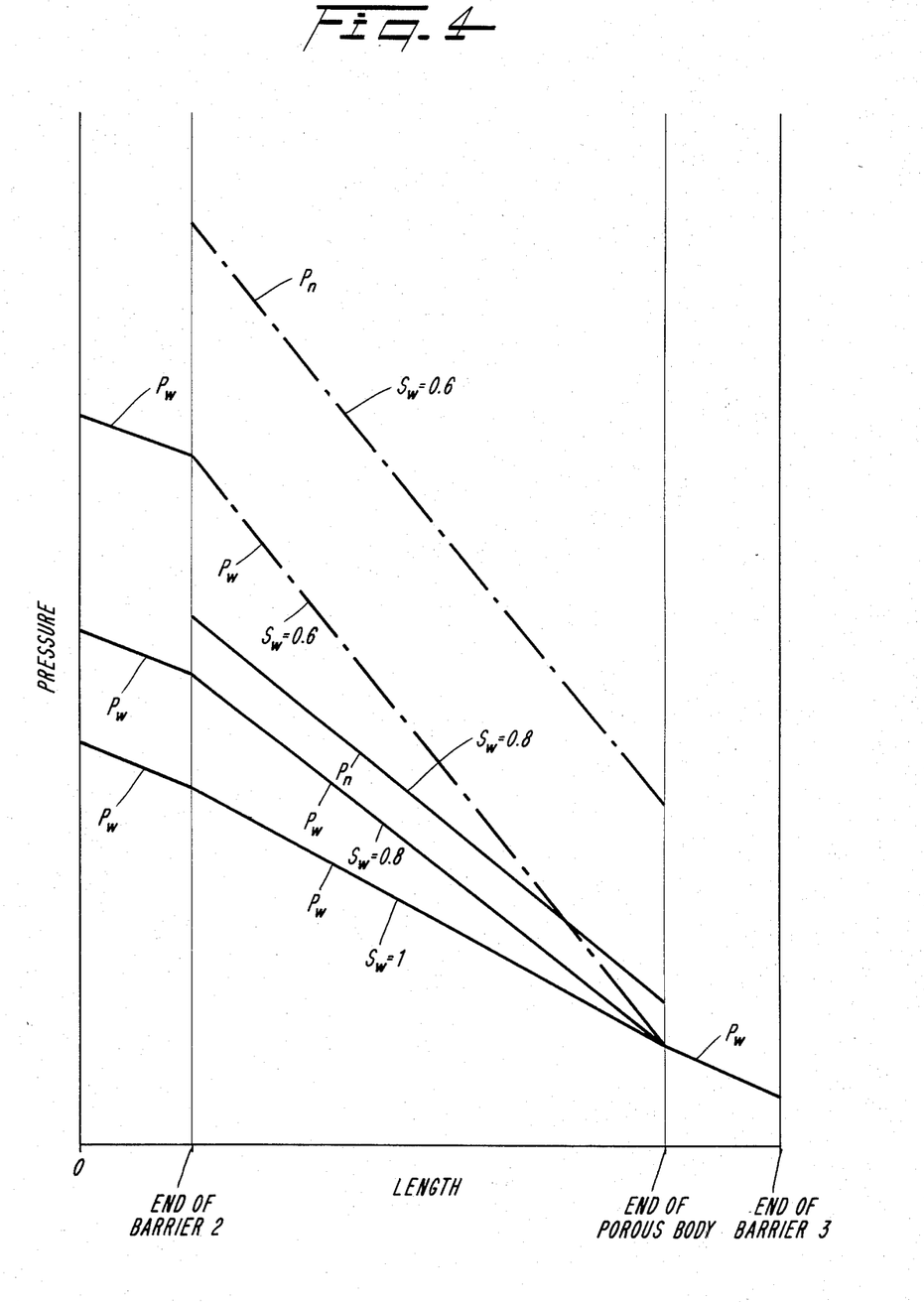
FIG. 4 is a graph of the pressure conditions prevailing at equilibrium within the porous barriers and porous body of the apparatus of FIG. 1.

As long as the capillary pressure is greater than the displacement pressure (Point A in FIG. 2), desaturation begins to occur, i.e., $S_w$ decreases, and this desaturation continues until an equilibrium interstitial distribution of wetting and nonwetting fluid is reached. Note that $S_w+S_n=1$. Equilibrium is reached when the pressure measured by transducer 8 stops climbing. If, as this pressure rises, the pressure of the nonwetting fluid as measured by transducer 10 is also increased by adjusting pressure regulator 13 to maintain the capillary pressure difference between the values read at transducers 10 and 8, a condition of uniform saturation distribution and capillary pressure is attained and sustained. FIG. 4 shows the resultant pressure conditions that will prevail at equilibrium for hypothetical fluids and porous body at a given saturation level.

At this point, the pressure drop measured by transducer 12 applies to both flowing fluid phases because the pressure drop across the two porous barriers for the wetting phase fluid remains constant. Flow rates $Q_w$ and $Q_n$ may be determined by the flow meters 7 and 15, thus there is enough information to calculate the points, B1, B2, B3 etc. on the capillary pressure curve (FIG. 2) and on the $K_w$, $K_n$ relative permeability curves (FIG. 3), provided the experimenter has an independent method to measure the saturation level, of the wetting fluid, $S_w$, or the nonwetting fluid, $S_n$, to which these curves apply. It is not necessary, for purposes of this invention, to keep the immiscible fluids in motion to maintain a final capillary equilibrium. Once such equilibrium is established, it will be maintained if both fluids are simultaneously stopped from flowing. It will be possible between consecutive equilibrium stages to stop the flow of both fluids, remove the porous sample, if necessary, and determine the saturation level independently by electrical conductivity, X-ray absorption, or other state of the art procedures, or a direct gravimetric procedure may be incorporated into the way this invention is routinely practiced. Note that a simple weight measurement is all that is required to calculate the saturation level as long as the porosity and the empty (dry) weight of the core sample are known and the fluid phase densities are also known.

If test specimen 1 has been removed from the apparatus, it may now be reintroduced and a new equilibrium may be established by adjusting regulators 13 and 14. At all times when fluid flows in this procedure, the wetting fluid flow rate, $Q_w$, must be constant, the wetting fluid pressure, $P_w$, measured at the outflow point of the wetting fluid, and the pressure difference between the pressure of the nonwetting fluid, $P_n$, measured at transducer 10 and $P_w$ measured at transducer 8 must be kept constant. Eventually, the entire drainage capillary pressure and relative permeability curves for a given capillary pressure may be generated by this procedure.

As the saturation level of the wetting fluid, Sw, for example, is lowered, the speed of pump 4 will need to be increased in order to maintain the value of Qw. The pressure measured at transducer 8 will also increase and the relative permeability, Kw, will become vanishingly small. Eventually the wetting fluid will not flow at all. In some cases, depending on the porous solid and fluids used, before this point is reached, pump 4 reaches the limit of its capacity, and measurement under a constant flow rate becomes impracticable. Under there circumstances, though continuing to lower the saturation level of the wetting phase is still theoretically possible, an end point must be assumed at the minimum wetting phase saturation level attainable on the apparatus. The measurement of the relative permeability of the nonwetting fluid, Kn, then becomes trivial. After establishing the end point of this procedure, plotted as Point (C) in the graphs of FIG. 2 and FIG. 3, the saturation level in the nonwetting phase is lowered by adjusting regulators 13 and 14, while still maintaining the capillary pressure difference between wetting and nonwetting fluids initially established for each experiment. Each time the pressure is lowered, a new equilibrium is reached as before, but this time Sw is increased at each step and the results are plotted as Point $D_1$, $D_2$ etc. in FIG. 2 and FIG. 3. Finally, an end point is reached where the nonwetting fluid flow rate, Qn, is equal to 0 and Kn also equals 0. Kw may now be measured when only one mobile phase is present, through nonwetting fluid is still within the porous body. This is plotted as Point E in the graphs of in FIG. 2 and FIG. 3. Since, nonwetting, nonmobile fluid remains in the porous body, Sw is less than 1.

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. An apparatus for determining data from which to calculate relative permeability of a porous body to a first fluid and a second fluid comprising:
   (a) means for rendering all but first and second outer surfaces of said porous body impermeable to said first and second fluids;
   (b) first and second capillary barriers respectively covering said first and second outer surfaces, said barriers being permeable to said first fluid and impermeable to said second fluid;
   (c) first fluid inlet means for flowing said first fluid under pressure to an outer surface of said first barrier and first fluid outlet means for conducting said first fluid away from an outer surface of said second barrier;
   (d) means for controllably changing said pressure in said first fluid;
   (e) means for maintaining constant the flow rate of said first fluid;
   (f) second fluid inlet means for flowing said second fluid under pressure to said first surface of said porous body and second fluid outlet means for conducting said second fluid away from said second surface of said porous body;
   (g) means for gauging the fluid pressure at said first fluid inlet means and at said first fluid outlet means;
   (h) means for maintaining constant the fluid pressure at said first fluid outlet means;
   (i) means for gauging the fluid pressure at said second fluid inlet means and at said second fluid outlet means; and
   (j) means for regulating fluid pressure at said second fluid inlet means and at said second fluid outlet means.

2. The apparatus of claim 1, wherein said first and second outer surfaces of said porous body comprise planar portions of a cylindrical porous body.

3. The apparatus of claim 1, wherein said means for rendering all but first and second outer surfaces of said porous body impermeable to said first and second fluids comprises:
   (a) a hollow metallic shell, complementary in shape to said porous body, equipped with openings over said first and second outer surfaces of said porous body, and equipped with a small hole for admitting a third fluid to the interior portion of said shell;
   (b) an elastic, impermeable lining for the inside of said hollow shell;
   (c) means for forcing a third fluid through said small hole and into the interstitial space between said metallic shell and said elastic, impermeable inside lining; and
   (d) a third fluid.

4. An apparatus for determining data from which to calculate the relative permeability to fluid flow of a porous body having a front side and a back side wherein said device comprises:
   (a) means for rendering all sides but said front side and said back side of said porous body impermeable to a first fluid and a second fluid;
   (b) a first porous barrier held in contact with said front side of said porous body, wherein said contact permits a first fluid to flow from said first porous barrier to said front side of said porous body;
   (c) a second porous barrier held in contact with said back side of said porous body, wherein said contact permits a first fluid to flow from said back side of said porous body to said second porous barrier;
   (d) a first fluid flow system in communication with said first porous barrier and said second porous barrier;
   (e) means for forcing a first fluid to flow through said first fluid flow system, said porous barriers, and said porous body;
   (f) means for measuring the pressure of said first fluid in said first fluid flow system before said first fluid encounters said first porous barrier;
   (g) means for measuring the pressure of said first fluid in said first fluid flow system after said first fluid leaves said second porous barrier;
   (h) means for regulating the pressure of said first fluid after said first fluid leaves said second porous element;
   (i) means for measuring the flow rate of said first fluid through said first fluid flow system;
   (j) means for regulating the flow rate of said first fluid through said first fluid flow system;
   (k) a second fluid flow system in communication with said front side of said porous body and said back side of said porous body;

(l) means for forcing said second fluid to flow through said second fluid flow system and said porous body;

(m) means for regulating the pressure of said second fluid before said second fluid enters said porous body;

(n) means for measuring the pressure of said second fluid before said second fluid enters said porous body;

(o) means for measuring the pressure of said second fluid after said second fluid leaves said porous body;

(p) means for regulating the pressure of said second fluid after said second fluid leaves said porous body; and (q) means for measuring the flow rate of said second fluid through said second fluid flow system.

5. The apparatus of claim 4, wherein said porous body is shaped like a cylinder.

6. The apparatus of claim 4, wherein said means for rendering all sides but said front side and said back side of said porous body impermeable to said first fluid and said second fluid comprises:

(a) a hollow metal shell complementary in shape to said porous body and equipped with openings over said front side and said back side of said porous body and equipped with a small hole for admitting a third fluid to the interior portion of said shell;

(b) an elastic, impermeable lining for the inside of said hollow shell;

(c) means for forcing a third fluid to flow through said orifice into interstitial space between said hollow cylinder and said lining; and (d) a third fluid.

7. The apparatus of claim 4, wherein said device further comprises:

(a) a prefilter for filtering said first fluid before said first fluid enters said first porous element.

8. The apparatus of claim 4, wherein said device further comprises:

(a) means for measuring the difference in pressure between said second fluid before said second fluid enters said porous body and said second fluid after said second fluid leaves said porous body.

9. The apparatus of claim 4, wherein said device further comprises:

(a) means for stopping said first fluid after said first fluid leaves said second porous element;

(b) means for stopping said second fluid before said second fluid enters said porous body; and (c) means for stopping said second fluid after said second fluid leaves said porous body.

10. The apparatus of claim 4, wherein said first fluid wets said porous barriers with respect to said second fluid.

11. The apparatus of claim 10, wherein said first fluid wets said porous body with respect to said second fluid.

12. The apparatus of claim 4, wherein said first fluid and said second fluid are substantially incompressible.

13. The apparatus of claim 1, wherein said first fluid wets said capillary barriers with respect to said second fluid.

14. The apparatus of claim 13, wherein said first fluid wets said porous body with respect to said second fluid.

15. A method for determining data from which to calculate the relative permeability of a porous body to first fluid flow and second fluid flow comprising the steps of:

(a) saturating said porous body with said first fluid;

(b) forcing said first fluid to flow under pressure through said porous body;

(c) establishing a constant pressure of said first fluid upon exiting said porous body;

(d) establishing a constant flow rate of said first fluid through said porous body;

(e) measuring the pressure of said first fluid before said first fluid enters said porous body;

(f) measuring the pressure of said first fluid after said first fluid leaves said porous body;

(g) flowing said second fluid under pressure through said porous body, while maintaining constant the pressure of said first fluid upon exiting said porous body and maintaining constant the flow rate of said first fluid through said porous body;

(h) measuring the pressure change of said first fluid across said porous body;

(i) determining the pressure of said second fluid before said second fluid enters said porous body;

(j) determining the pressure of said second fluid after said second fluid exits porous body;

(k) measuring the flow rate of said second fluid through said porous body;

(l) measuring the saturation level of said second fluid;

(m) increasing the saturation level of said second fluid;

(n) repeating steps (g) through (m) until the saturation level of said second fluid is sufficiently high that maintaining said first fluid flow rate becomes impracticable;

(o) decreasing the saturation level of said second fluid; and (p) repeating steps (g) through (l) and (o) until the flow rate of said second fluid equals zero.

16. A method for determining data from which to calculate the relative permeability of a porous body to first fluid flow and second fluid flow comprising the steps of:

(a) inserting said porous body between a first porous barrier and a second porous barrier with capillary contact therebetween;

(b) saturating said porous body and said porous barriers with a first fluid;

(c) driving said first fluid continuously through said porous body and said porous barriers at a constant flow rate;

(d) measuring the difference between the pressure of said first fluid before entering said first porous barrier and the pressure of said first fluid after leaving said second porous barrier;

(e) measuring the difference between the pressure of said first fluid before entering said porous body and the pressure of said first fluid after leaving said porous body;

(f) forcing a second fluid to flow under pressure at a low saturation level through said porous body;

(g) employing a stepwise capillary pressure desaturation process;

(h) measuring the minimum saturation level of said first fluid;

(i) employing a stepwise capillary imbibition process; and (j) determining the minimum saturation level of said second fluid.

17. The method of claim 16, wherein said stepwise capillary pressure desaturation process comprises the steps of:

(a) flowing said second fluid under pressure through said porous body at a constant flow rate;
(b) maintaining said constant flow rate of said first fluid;
(c) establishing and maintaining at a constant value the pressure of said first fluid after leaving said second porous barrier;
(d) establishing a desired capillary pressure difference between the pressure of said second fluid before entering said porous body and the pressure of said first fluid before entering said first porous barrier;
(e) determining the saturation level of said second fluid;
(f) increasing the saturation level of said second fluid; and
(g) repeating steps (b), (c), (d), (e), and (f) until maintaining the constant flow rate of said first fluid becomes impracticable.

18. The method of claim 16, wherein said stepwise capillary imbibition process comprises the steps of:
(a) maintaining the constant flow rate of said first fluid;
(b) maintaining the pressure of said first fluid after leaving said second porous barrier;
(c) establishing and maintaining a desired capillary pressure difference between the pressure of said second fluid before entering said porous body and the pressure of said first fluid before entering said first porous barrier;
(d) determining the saturation level of said first fluid;
(e) increasing the saturation level of said first fluid; and
(f) repeating steps (a), (b), (c), (d), and (e) until said second fluid stops flowing through said porous body.

19. The method of claim 17, wherein said stepwise capillary imbibition process comprises the steps of:
(a) maintaining the constant flow rate of said first fluid;
(b) maintaining the pressure of said first fluid after leaving said second porous barrier;
(c) establishing and maintaining a desired capillary pressure difference between the pressure of said second fluid before entering said porous body and the pressure of said first fluid before entering said first porous barrier;
(d) determining the saturation level of said first fluid;
(e) increasing the saturation level of said first fluid; and
(f) repeating steps (a), (b), (c), (d), and (e) until said second fluid stops flowing through said porous body.

20. The method of claim 16, wherein said first fluid wets said porous body with respect to said second fluid.

21. The method of claim 20, wherein said first fluid wets said porous body with respect to said second fluid.

22. The method of claim 16, wherein said second fluid said second fluid are substantially incompressible.

* * * * *